United States Patent [19]

Kim et al.

[11] Patent Number: 5,089,621

[45] Date of Patent: Feb. 18, 1992

[54] DIAZABICYCLO AMINE COMPOUNDS WHICH ARE INTERMEDIATES FOR ANTI-BACTERIAL COMPOUNDS

[75] Inventors: Wan J. Kim; Myung H. Park, both of Yuseong; Jong H. Oh, Seo, all of Rep. of Korea

[73] Assignee: Korea Research Institute of Chemical Technology, Daejeon, Rep. of Korea

[21] Appl. No.: 598,888

[22] Filed: Oct. 19, 1990

[30] Foreign Application Priority Data

Oct. 23, 1989 [KR] Rep. of Korea .................. 89-15204

[51] Int. Cl.$^5$ .................. C07D 487/04; C07D 471/04
[52] U.S. Cl. .................................. 546/113; 540/580; 546/122; 548/453
[58] Field of Search ................ 540/580; 546/113, 122; 548/453

[56] References Cited

U.S. PATENT DOCUMENTS 4,988,709   1/1991   Ogata et al. .................. 546/156

*Primary Examiner*—Bernard Dentz
*Attorney, Agent, or Firm*—Finnegan, Henderson, Farabow, Garrett, and Dunner

[57] ABSTRACT

Diazabicycloamine compounds of the general formula I and their acid salts

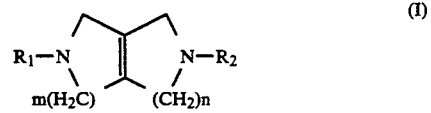

(I)

wherein
m represents an integer of 1 to 3,
n represents 1 or 2, and
$R_1$ or $R_2$ represents hydrogen or lower alkyl group, a process for their manufacture and their use for the preparation of novel quinolone compounds having excellent antibacterial activity.

2 Claims, No Drawings

DIAZABICYCLO AMINE COMPOUNDS WHICH ARE INTERMEDIATES FOR ANTI-BACTERIAL COMPOUNDS

The present invention relates to new diazabicyclo compounds of the following general formula I

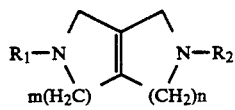

wherein
m represents an integer of 1 to 3
n represents 1 or 2, and
$R_1$ or $R_2$ represents hydrogen or lower alkyl and their salts.

The compounds can be used for the preparation of novel quinolone compounds having excellent antibacterial activity and can also be used for the preparation of novel cephalosporines and other pharmaceutically interesting compounds. The invention relates further to a process for their preparation.

Since the first introduction of nalidixic acid as a chemotherapeutic agent for urethritis, many quinolone antibacterial agents, especially norfloxacin, ciprofloxacin and ofloxacin are being widely used in hospitals nowadays in a variety of indications.

However, whereas these quinolone antibacterial agents have a high antibacterial activity against Gram negative bacteria, these agents have a disadvantage due to their lower antibacterial activity against Gram positive bacteria, such as Staphylococcus spp. or Streptococcus spp.

As result of the effort to solve the problems of the existing quinolone antibacterial agents, the following facts have been discovered and have led to the present invention. The novel quinolone antibacterial agents are prepared by introducing the diazabicycloamine compound of the general formula I onto the C-7 or C-10 position of the quinoline nuclei shown in the following general formula (A) or (B) as a substituent $R_3$

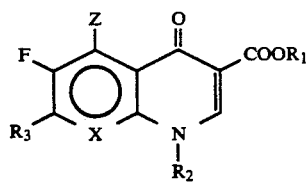

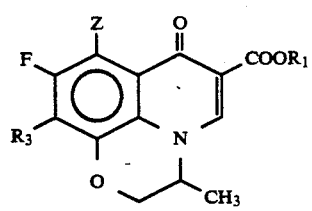

wherein in (A) and (B)
X represents C-H, C-F or N,
Z represents hydrogen, halogen or amino,
$R_1$ represents hydrogen or a pharmaceutically acceptable cation,
$R_2$ represents alkyl, halogenated alkyl or hydroxyalkyl having 1 to 4 carbon atoms, vinyl or cycloalkyl having 3 to 6 carbon atoms,
$R_3$ represents the introduced group corresponding to the above general formula I.

While the existing quinolone compounds have only a low antibacterial activity against Gram positive bacteria, the novel quinolone compounds have an excellent antibacterial activity not only against Gram negative bacteria but also against Gram positive bacteria.

The detailed description of the present invention is as follows.

The present invention consists of the diazabicycloamine compounds of the following general formula I and their acid addition salts

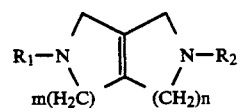

wherein
m represents an integer of 1 to 3,
n represents 1 or 2, and
$R_1$ or $R_2$ represents hydrogen or lower alkyl group.

Preferred are diazabicycloamines of the formula I, wherein m denotes 1 or 2, n denotes 1 and $R_1$ and $R_2$ denote hydrogen or lower alkyl, with the proviso that $R_1$ and $R_2$ cannot be lower alkyl simultaneously. These preferred compounds can also be represented by the general formula Ie

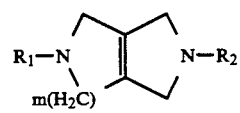

wherein m is 1 or 2 and one of $R_1$ and $R_2$ is lower alkyl whereas the other one is hydrogen.

The term "lower alkyl" means alkyl with 1-4 carbon atoms, preferably methyl and ethyl.

The present invention relates also to a process for the manufacture of diazabicycloamines of the formula I and their salts

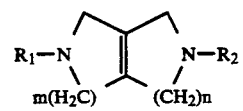

wherein
m denotes 1 to 3,
n denotes 1 to 2 and
$R_1$ and $R_2$ denote hydrogen or lower alkyl which comprises
(a) reacting tetrakis(halomethyl)ethylene with ammonia, whereby a compound of the formula I with m and n=1 and $R_1$ and $R_2$=hydrogen is obtained
(b) removing from a compound of the formula I, wherein one or both nitrogen atoms are protected, the protecting group(s) and—if desired—alkylating one or both nitrogen atoms,
(c) removing from a compound of the formula I, wherein one nitrogen atom bears an alkyl group and the other nitrogen atom is protected, the protecting group, or (d) reducing a merimine derivative of the formula

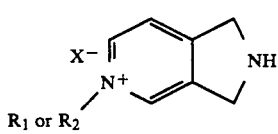

wherein $R_1$ or $R_2$ is lower alkyl and $X^{(-)}$ is an anion, as e.g. $Br^{(-)}$ or $Cl^{(-)}$.

The term "halo" in variant (a) means chloro, bromo or iodo, preferably bromo.

Preferred is the process for the manufacture of diazabicycloamines of the formula I and their salts

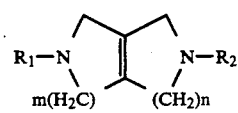

wherein m denotes 1 or 2, n denotes 1 and $R_1$ and $R_2$ denote hydrogen or lower alkyl with the proviso that $R_1$ and $R_2$ cannot be lower alkyl simultaneously, which consists of the same variants (a) to (d) with exception of the dialkylation in variant (b).

The reaction variant (a) is described below in detail.

As protecting groups in variants (b) and (c), in principle each N-protecting group known from literature, e.g. in the field of peptide or β-lactam chemistry, may be used which can easily be split off in conventional manner, i.e. by solvolysis, including hydrolysis, hydrogenolysis or by reduction.

As examples for protecting groups removable by solvolysis may be mentioned arylsulfonyl, such as p-toluenesulfonyl or phenylsulfonyl; or alkoxycarbonyl such as ethoxy-, t-butoxy-or benzyloxycarbonyl.

The removal of these protecting groups may be carried out in well-known manner in an appropriate solvent between about 0° C. and elevated temperatures, e.g. up to 160° C., in the presence of an acid, such as e.g. hydrochloric or hyrobromic acid, sulfuric acid, acetic acid, trifluoroacetic acid or formic acid, or in the presence of a base, such as e.g. sodium or potassium hydroxide, sodium or potassium carbonate or sodium acetate. As solvent water can be used, or—if necessary—also an organic solvent, such as e.g. ethanol, dioxane or acetic acid, alone or in mixture with water.

Examples for protecting groups removable by hydrogenolysis are benzyl or substituted benzyl; or arylsulfonyl, such as p-toluenesulfonyl or phenylsulfonyl.

These groups can be split off in customary manner known from literature under different conditions, e.g. in a hydrogen stream in an inert solvent at room temperature or slightly elevated temperatures in the presence of a catalyst, as e.g. platinum, palladium or Raney nickel; or with e.g. zink in acetic acid or methanol.

It is also possible to remove protecting groups such as e.g. toluenesulfonyl or phenylsulfonyl by reduction, as for instance by $NaAlH_2(OCH_2CH_2OCH_3)_2$.

Because compounds of the formula I wherein $R_1$ and/or $R_2$ is a protecting group are preferably obtained—as described below—by a cyclization reaction which can be generalized as follows

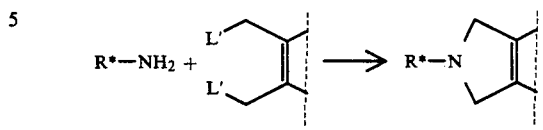

($R^*$ = protecting group, $L'$ = leaving group)

protecting groups which can be introduced together with the nitrogen atom are therefore preferred, such as for instance arylsulfonyl, as e.g. p-toluenesulfonyl, or alkylsulfonyl as e.g. methanosulfonyl (both introduced in form of the corresponding sulfonamide), alkoxycarbonyl, e.g. ethoxycarbonyl (introduced as the corresponding urethane) or acetyl (introduced as acetamide), preferably p-toluenesulfonyl.

Some preferred removal conditions can be described as follows. The removal of e.g. toluenesulfonyl may be carried out for example with hydrobromic acid, e.g. 48% hydrobromic acid in the presence of phenol and refluxing for e.g. 3-5 hours, the removal of e.g. ethoxycarbonyl with hydrochloric acid, preferably 20% hydrochloric acid, and the removal of e.g. the benzyl group by hydrogenolysis in acetic acid solution with 10% Pd-charcoal/hydrogen, preferably with stirring or refluxing for some hours.

If two protecting groups are to be split off selectively, it is advisable to use one group which can be split off under acid conditions, as e.g. toluenesulfonyl, whereas the other one can be removed by hydrogenolysis, as e.g. benzyl. Thus, toluenesulfonyl can first be removed e.g. by hydrobromic acid and then benzyl subsequently e.g. by Pd-charcoal/hydrogen.

If an N-alkylation of the compounds of the formula I is to be carried out, the alkyl group can be introduced by conventionyl methods, e.g. with an alkyl halide, for example ethyl iodide in an inert solvent, e.g. in dimethyl formamide in the presence of a base, e.g. potassium carbonate, preferably at lower temperatures, e.g. at room temperature and a reaction time of up to about 24 hours.

A methyl group can for example be introduced by the reaction with formaline, preferably 35-37% aqueous formaline, and formic acid, preferably under reflux for some hours, e.g. for about 2 to 6 hours.

When a dimethylation or a methylation of a mono-N-protected compound is intended, an excess of formalin/formic acid is used, whereas the monomethylation of an unprotected compound of the formula I requires the use of an about equivalent amount of the methylation agent.

The reduction of a merimine, mentioned in the above variant (d) can be carried out in a conventional manner as described in literature for this type of compounds. Thus, hydrogenation can for instance be applied, preferably with Pd/charcoal in an inert solvent, such as a lower alcohol, e.g. methanol or ethanol.

The following more detailed processes are also a part of our invention:

The present invention includes also a process for the preparation of the free diazabicycloamine compound of the following general formula (Ia)

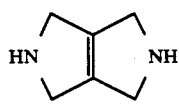

(Ia)

characterized by heating tetrakis (halomethyl)ethylene, wherein halo is as defined above, and liquid ammonia under increased pressure.

The present invention relates further to a process for the preparation of acid salts of the diazabicycloamine compound of in the following general formula (Ib)

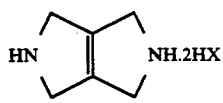

(Ib)

wherein X represents the anion of an acid, preferably chlorine or bromine, characterized by cyclizing tetrakis(halomethyl)ethylene, wherein halo is as defined above, with 2 mols, preferably a slight excess of a compound of the formula R*—$NH_2$, wherein R* is a nitrogen-protecting group, such as e.g. methansulfonyl, acetyl or alkoxycarbonyl, e.g. ethoxycarbonyl, preferably toluenesulfonyl, in a polar solvent in the presence of a base, and then removing the nitrogen-protecting group, for instance by treatment with an acid. Preferred examples for the compound R*—$NH_2$ are methanesulfonamide, acetamide or an urethane, preferably p-toluene sulfonamide.

The present invention relates also to a method for the preparation of the diazabicycloamine compound of the following formula (Ic)

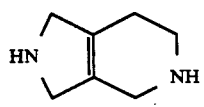

(Ic)

which is characterized by the following steps:

(A) A 3-pyrroline compound is prepared by cyclization of tetrakis(halomethyl)ethylene, wherein halo is as defined above, and 1 mol, preferably a slight excess of a compound of the formula R*—$NH_2$, wherein R* is as defined above, preferably p-toluene sulfonamide, in a polar solvent in the presence of a base, (B) one of the two halogens, preferably bromines, of the compound is substituted by a cyanide group, (C) this cyanide group is reduced to the aminomethyl group, (D) a nitrogen protected 3,8-diazabicyclo[4.3.0]non-1(6)-ene is then obtained by cyclizing the compound of step (C) in the presence of a base, and then the protecting group is removed in the presence of an acid or by hydrogenolysis which leads to the compound Id, or (E) a second protecting group selectively removable, e.g. by hydrogenolysis, is introduced to the secondary amine of the above nitrogen protected 3,8-diazabicyclo[4.3.0]non-1(6)-ene, the first protecting group, e.g. the paratoluenesulfonyl group is selectively removed by acid and the second protecting group is removed by hydrogenolysis under acidic conditions, or vice versa, and the acid addition salt of the following formula (Id)

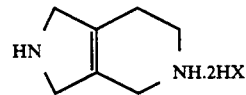

(Id)

wherein X represents the anion of an acid, preferably chlorine or bromine, is obtained and which may then be treated with alkali to give (Ic)

The following description is a still more detailed disclosure of the present invention.

Among the diazabicycloamine compounds according to the present invention, the free diazabicycloamine compound of the above formula (Ia), the 3,7-diazabicyclo[3.3.0]oct-1(5)-ene, can e.g. be prepared by adding the well known tetrakis(bromomethyl)ethylene [compound (1) of the reaction scheme] [reference: (1) A. C. Cope, et al., J. Am. Chem. Soc., 80, 5499 (1958), (2) P. W. LeQuesne, et al., J. Org. Chem., 40, 142 (1975)] to the mixture of a solvent, for example a lower alcohol, e.g. methanol, and liquid ammonia, and then heating the reaction mixture in a sealed tube under increased pressure for several hours, for example for about 8 hours in an oil bath of about 180° C.

The acid salt of the diazabicycloamine compound of the above general formula (Ib) can e.g. be prepared by cyclization of tetrakis(bromomethyl)ethylene [compound (1)] and p-toluene sulfonamide, methanesulfonamide, acetamide or an urethane in a polar solvent, as e.g. dimethylformamide in the presence of a base, as e.g. potassium carbonate or sodium hydroxide, preferably at room temperature, followed by heating the cyclized compound in the presence of an acid to remove the nitrogen-protecting groups. Preferred for the removal is the use of hydrobromic acid, e.g. 48% hydrobromic acid in the presence of phenol and refluxing of this mixture for several hours, for example 4 hours.

The diazabicycloamine compound of the formula (Ic), the 3,8-diazabicyclo[4.3.0]non-1(6)-ene, can be prepared by the following steps.

First, a 3-pyrroline compound [compound (3)] is prepared e.g. by cyclization of tetrakis(bromomethyl)ethylene [compound (1)] and p-tuoluene sulfonamide in the presence of a solvent, e.g. dimethylformamide in the presence of a base, e.g. potassium carbonate, and then the cyanide group is substituted for one of the two bromine atoms by addition of a cyanide, preferably sodium cyanide, to the refluxed solution, e.g. in dimethylsulfoxide, which leads to compound (4). The aminoethyl compound [compound (5)] is obtained by the reduction of the cyanide group, for example with lithium aluminum hydride, and the nitrogen-protected 3,8-diazabicyclo[4.3.0]non-1(6)-ene derivative [compound (6)] is then prepared by cyclizing this compound for example in dimethylformamide solution, by addition of e.g. anhydrous potassium carbonate, prefarably at room temperature and stirring for several hours. Thereafter, the compound (7) can be obtained by introducing a second protecting group, for example a benzyl group by adding benzylbromide in the presence of a base, e.g. of sodium hydroxide, to the secondary amine of the compound (6). The compound (8) is then prepared by removing selectively the first protecting group with acid for example with hydrobromic acid, preferably 48% hydrobromic acid in the presence of phenol under reflux for several hours. The acid salt of the general formula (Id) is obtained by removing the protecting group of the above compound (6) in the presence of an acid, preferably of 48% hydrobromic acid in the presence of phenol and refluxing for several hours, or by removing the second protecting group of the above compound (8) by hydrogenolysis under acidic condition, e.g. under reflux for several hours in acetic acid solution in the presence of 10% Pd-charcoal under hydrogen stream. Then the diazabicycloamine of the formula (Ic) is obtained by treating the compound of the formula (Id) with alkali in usual manner.

In the above steps, each protecting group can—as already described above—be removed for instance by using an acid, e.g. hydrobromic or hydrochloric acid, by alkali such as e.g. sodium hydroxide and potassium hydroxide, Na/NH$_3$ or by hydrogenolysis.

The above described reactions can be summarized in the following reaction scheme using especially the preferred substituents:

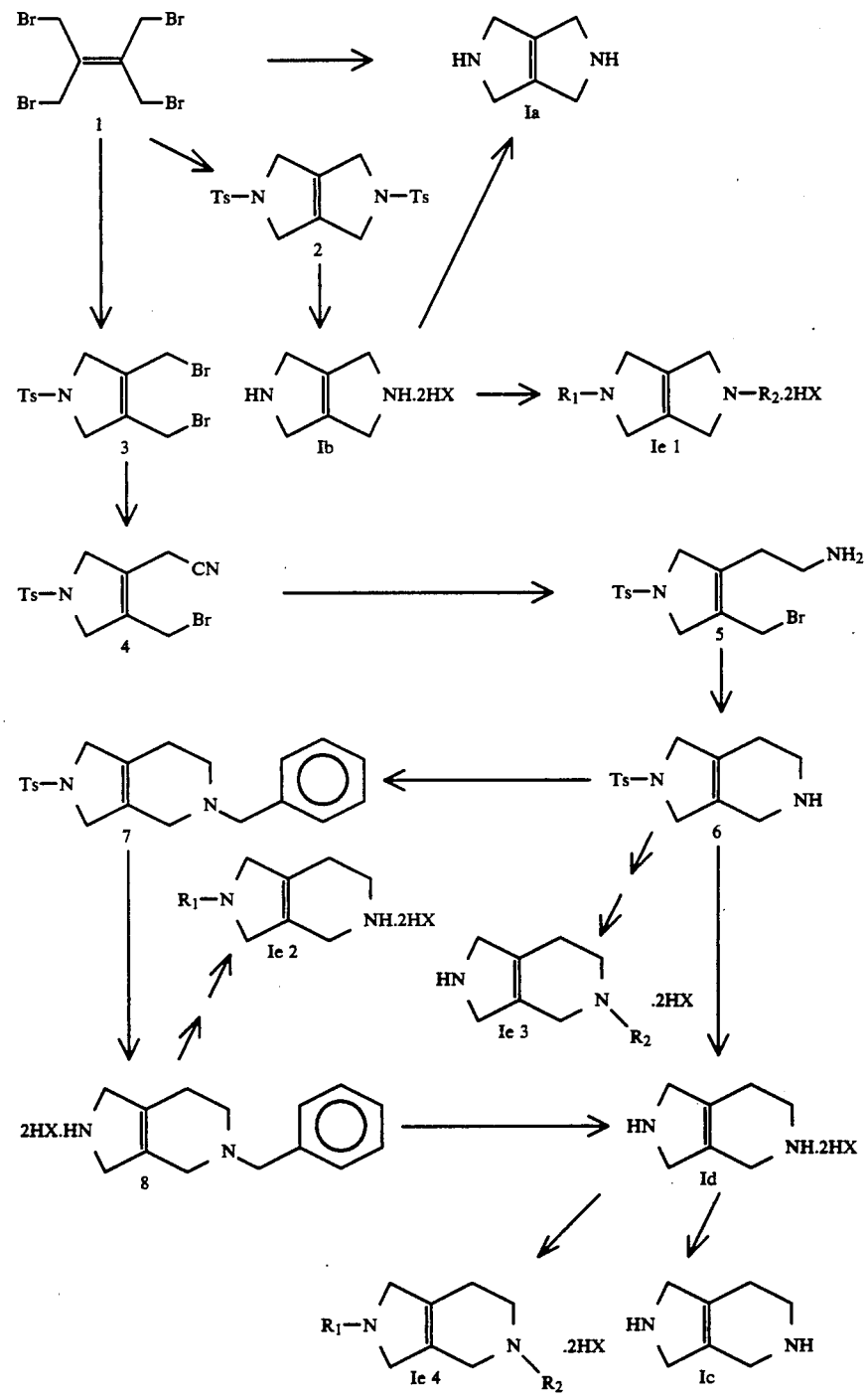

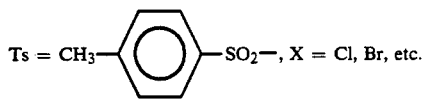

Compounds of the general formula I, wherein m=2 and n=1 can also be prepared by reduction of a merimine derivative of the following formula

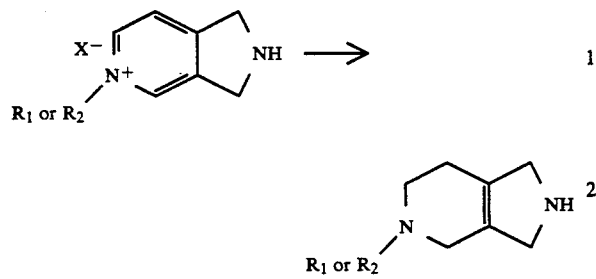

wherein $X^{(-)}$ is an anion, e.g. $Br^{(-)}$ or $Cl^{(-)}$ and $R_1$ or $R_2$ is lower alkyl, under the above described conditions.

Monoalkyl-3,8-diazabicyclo[4.3.0]non-1(6)-ene compounds such as compounds (Ie2) or (Ie3) can also be prepared by alkylation of the intermediate (8) or (6), followed by deprotection, using the methods and conditions already described above.

An alternative way to obtain compounds of the type (Ic) or (Id) is the hetero-Diels-Alder reaction of 2,3-bis(-halomethyl)-1,3-butadiene with methylenediurethane (methylenebiscarbamate) in the presence of a Lewis acid, cyclization with an appropriate amine R—NH$_2$ under basic conditions as exemplarily described below and deprotection, e.g. with hydrochloric acid:

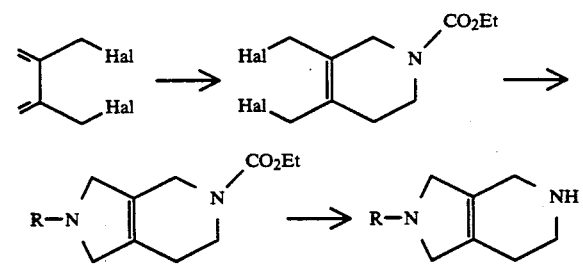

wherein Hal is chlorine, bromine or iodine, preferably bromine and R is lower alkyl or optionally also a protecting group.

Alkylated diazabicycloamine compounds of the general formula I, especially the preferred ones, can also be prepared by N-mono- or N-di-alkylation of compounds of the general formulae (Ia), (Ib), (Ic) or (Id), using the methods and conditions already described above.

Another way of preparation of N-monoalkyl 3,7-diazabicyclo[3.3.0]oct-1(5)-ene is the cyclization of the N-protected, preferably of the 1-p-toluenesulfonyl-3,4-bis(halomethyl)3-pyrroline, wherein halo is as described above, with appropriate alkylamines, e.g. methyl- or ethylamine, under basic conditions, e.g. in the presence of anhydrous potassium carbonate, followed by deprotection, e.g. by hydrolysis with acids, for example with hydrobromic acid/phenol. The reaction scheme with the preferred substituents is as follows:

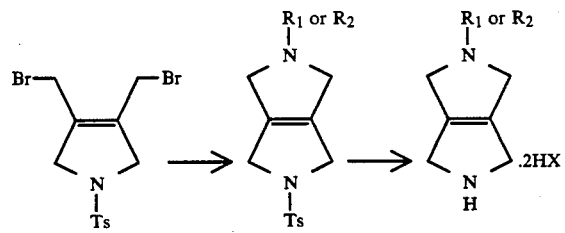

wherein
$R_1$ or $R_2$ represents lower alkyl, and
X represents preferably chlorine or bromine.
The following examples are to illustrate, but not to limit the invention.

EXAMPLES

EXAMPLES 1

Preparation of 3,7-bis-p-toluenesulfonyl-3,7-diazabicyclo [3.3.0] oct-1(5)-ene 30 g of tetrakis (bromomethyl)ethylene and 30 g of p-toluene sulfonamide were dissolved in 400 ml of dimethylformamide. 150 g of potassium carbonate anhydride (or 50% sodium hydride 17 g) was added and then stirred at room temperature for 24 hours. Thereafter, this reaction mixture was distilled under vacuum to remove solvents. By adding 30 ml of water and 100 ml of ethylacetate, 17 g of the title compound was obtained as pale yellow powder (yield 50%).

Melting point: 250° C (dec.).

$^1$H-NMR (DMSO-d$_6$,δ ppm):7.65 (4H, d, J=8.08 Hz), 7.39 (4H, d, J=8.08 Hz), 3.94 (8H, s), 2.40 (6H, s).

ELMS : m/z418 (M$^{30}$, 1.3%),m/z 419 (M+1,1.2%).

EXAMPLES 2

Preparation of 3,7-diazabicyclo[3.3.0]oct-1(5)-ene dihydrobromide 60 ml of 48% hydrobromic acid and 7 g of phenol were added to 10.8 g 3,7bis-p-toluenesulfonyl-3,7-diazabicyclo[3.3.0]oct-1-(5)-ene, prepared in Preparation 1. The mixture was refluxed for 4 hours and cooled to room temperature. The aqueous phase was separated by adding 100 ml of chloroform and 50 ml of water. The aqueous phase was washed with chloroform (100 ml×4) and decolorized with active carbon. The aqueous phase was concentrated under vacuum and the remained solid was washed with 1:1 methanol-ethyl ether solvent. 5 g of the title compound was obtained as white solid (yield 71%).

Melting point: 220° C.(dec).

$^1$H-NMR (DMSO-D$_2$O,δ ppm): 4.06(8H, s).

MS: m/z 110(M+).

EXAMPLES 3

Preparation of 3,7-diazabicyclo[3.3.0]oct-1(5)-ene 2.72 g of 3,7diazabicyclo[3.30]oct-1(5)-ene dihydrobromide, prepared in Preparation 2, was added to 10 ml of 10% aqueous sodium hydroxide solution. The mixture was concentrated under reduced pressure to remove water, and then extracted with ether several times and concentrated. 1 g of the title compound was obtained (yield 90%).

$^1$H-NMR (D$_2$O,δ ppm): 4.02 (8H, s).
MS: m/z 110 (M+).

EXAMPLES 4

Preparation of 3,7-diazabicyclo[3.3.0]oct-1(5)-ene 0.7 g of tetrakis (bromomethyl)ethylene was dissolved in 10 ml of methanol and 4 ml of liquid ammonia and sealed and heated in 180° C. oil bath for 8 hours. After cooling the reaction mixture to room temperature, ammonia was evaporated. The mixture was concentrated to remove methanol. 10 ml of absolute ethanol was added and the undissolved compound was filtered off to remove insoluble material. Ethanol was removed by vacuum distillation. 3 ml of 30% aqueous potassium hydroxide solution was added to the oil residue. The solution was extracted with tetrahydrofuran (THF, 5 ml×3) and the obtained extrates were combined and dried (Na$_2$SO$_4$), concentrated to give 60 mg of the title compound (yield 31%).

$^1$H-NMR (DMSO-d$_6$,δ ppm): 4.04 (8H, s).
MS: m/z 110 (M+).

EXAMPLE 5

Preparation of N-(p-toluenesulfonyl)-3,4-bis(bromomethyl) -3-pyrroline 19 g of tetrakis (bromomethyl)ethylene and 9 g of p-toluene sulfonamide were dissolved in 220 ml of dimethylformamide. 30 g of anhydrous potassium carbonate was added and then stirred at room temperature for 20 hours. Thereafter solvent was removed by vacuum distillation. 50 ml of ethylacetate was added to obtain solid product, and solid product was purified by silica gel column chromatography. 12 g of the title compound was obtained (yield 60%).

Melting point : 170° C.
$^1$H-NMR (CDCL$_3$, δ ppm): 7.69 (2H, d, J=8.2 Hz), 7.33 (2H, d, J=8.2 Hz), 4.00 (4H, s), 3.15 (4H, s), 2.44 (s, 3H).

EXAMPLE 6

Preparation of N-(p-toluenesulfonyl)-3-(bromomethyl)-4-(cyanomethyl)-3-pyrroline 10 g of N-(p-toluenesulfonyl)-3,4-bis(bromomethyl)-3-pyrroline, prepared in Preparation 5, was dissolved in 10 ml of dimethylsulfoxide (DMSO) and then heated in oil bath for 2 hours with refluxing. During the heating and refluxing, 1.5 g of sodium cyanide was added by small portion. The reaction mixture was cooled to room temperature and poured into ice water and then extracted with methylene chloride (200 ml×3). The extracts were combined, dried over Na$_2$SO$_4$ and concentrated. The residue was purified by silica gel column chromatography. 5 g of the title compound was obtained (yield 57%).

Melting point: 182° C.
$^1$H-NMR (CDCl$_3$,δ ppm): 7.71 (2H, d, J=8.2 Hz), 7.36 (2H, d, J=8.2 Hz), 4.01 (4H, s), 3.20 (2H, s), 3.06 (2H, s), 2.45 (3H, s).

EXAMPLE 7

Preparation of N-(p-toluenesulfonyl)-3-(aminoethyl)-4-(bromomethyl)-3-pyrroline 4 g of N-(p-toluenesulfonyl)-3-(bromomethyl)4-(cyanomethyl)-3-pyrroline, prepared in Preparation 6, was dissolved in 100 ml of ethyl ether. The solution was slowly added to the suspension of 1 g of lithium aluminum hydride (LAH) in 20 ml of ethyl ether, and heated with refluxing for 3 hours. The reaction mixture was cooled by ice water. After adding 3 ml of water, it was stirred for 30 minutes and filtered off. The filtrate was concentrated. 2 g of the title compound was obtained (yield 49%).

Melting point: 185° C.
$^1$H-NMR (CDCl$_3$,δ ppm):7.84 (2H, d, J=8.2 Hz), 7.46 (2H, d, J=8.2 Hz), 4.20 (2H, g, J=7 Hz), 4.06 (4H, s), 2.45 (3H, s), 2.26 (2H, t, J=7 Hz).

EXAMPLE 8

Preparation of N$^8$-(p-toluenesulfonyl)-3,8-diazabicyclo[4.3.0]non-1(6)-ene 3.6 g of N$^1$-(p-toluenesulfonyl)-3-(aminoethyl)-4-(bromomethyl-3-pyrroline, prepared in Preparation 7, was dissolved in 30 ml of dimethylformamide. 5 g of anhydrous potassium carbonate was added to the solution and then stirred at room temperature for 18 hours. After concentrating the reaction mixture under reduced pressure to remove solvent, the mixture was extracted with methylene chloride (50 ml×3). After mixing the obtained extracts, it was washed with water and concentrated. 2.5 g of the title compound was obtained (yield 88%).

Melting point: 201° C.
$^1$H-NMR (CDC$_3$,δ ppm): 7.80 (2H, d, J=8.2 Hz), 7.44 (2H, d, J=8.2 Hz), 4.05 (4H, s), 3.41 (2H, s), 2.92(2H, t, J=5.8 HZ), 2.44 (2H, t, J=5.8 Hz).

EXAMPLE 9

Preparation of N$^3$-(benzyl)-N$^8$-(p-toluenesulfonyl)-3,8-diazabicyclo[4.3.0]non-1(6)-ene 1.8 g of N$^8$-(p-toluenesulfonyl)-3,8-diazabicyclo[4.3.0]non-1(6)-ene, prepared in preparation 8, was dissolved in 30 ml of methanol. 6 ml of 50% aqueous sodium hydroxide solution and 1.5 ml of benzyl bromide were added to the solution and stirred at room temperature for 5 hours. The reaction mixture was concentrated under reduced pressure to remove methanol and then extracted with methylene chloride (30 ml×3). It was dried (Na$_2$SO$_4$) and concentrated and then dried under reduced pressure. 2 g of the title compound was obtained (yield 85%).

Melting point: 196° C.
$^1$H-NMR (CDCl$_3$,δ ppm): 7.80 (2H, d, J=8.2 Hz), 7.44 (2H, d, J=8.2 Hz), 7.28 (5H, br. s), 4.01 (4H, s), 3.56 (2H, s), 3.40 (2H, s), 2.90 (2H, d, J=5.8 Hz), 2.22 (2H, t, J=5.8 Hz).

EXAMPLE 10

Preparation of N$^3$-(benzyl)-3,8-diazabicylclo[4.3.0]non-1(6)-ene hydrobromide 2 g of N$^3$-(benzyl)-N$^8$-(p-toluenesulfonyl)-3,8-diazabicyclo[4.3.0]non-1(6)-ene, prepared in Preparation 9, was suspended in 15 ml of 48% hydrobromic acid and 1.5 g of phenol, and the reaction mixture was refluxed for 3 hours. After cooling the reaction mixture, 20 ml of water was added the mixture was washed with chloroform (50 ml×3). The aqueous phase was taken and decolorized by active carbon. The aqueous phase was concentrated under reduced pressure and thus resulting solid was washed with 1:1 methanol-ethylether solvent. 1.5 g of the title compound was obtained (yield 98%).

Melting point: 205° C.(dec.).

$^1$H-NMR (CDCl$_3$,δ ppm): 7.29 (5H, br. s). 4.00 (4H, s), 3.55 (2H, s), 3.38 (2H, s), 2.91 (2H, d, J=5.8 Hz), 2.24 (2H, t, J=5.8 Hz).

EXAMPLE 11

Preparation of
3,8-diazabicyclo[4.3.0]non-1(6)-ene.dihydrobromide 1.5 g of N$^8$-(p-toluenesulfonyl)-3,8-diazabicyclo[4.3.0]non-1(6)-ene, prepared in Preparation 8, was suspended in 15 ml of 48% hydrobromic acid and 2 g of phenol, and the reaction mixture was refluxed for 4 hours. After cooling the reaction mixture, 20 ml of water was added. The mixture was washed with chloroform (40 ml×3). The aqueous phase was taken and decolorized by active carbon. The aqueous phase was concentrated under reduced pressure and thus resulting solid was washed with 1:1 methanol-ethylether solvent. 0.9 g of the title compound was obtained (yield 98%).

Melting point: 225°~227° C.(dec.).

EXAMPLE 12

Preparation of
3,8-diazabicyclo[4.3.0]non-1(6)-ene.dihydrobromide 0.7 g of N$^3$-(benzyl)-3,8-diazabicyclo[4.3.0]non-1(6)-ene hydrobromide, prepared in Preparation 10, was dissolved in 20 ml of 5% aqueous acetic acid solution. 0.5 g of 10% palladium charcoal in this solution was suspended and the reaction mixture was refluxed under the hydrogen stream for 7 hours. The solid was filtered off. The filtrate was concentrated under reduced pressure and dissolved in 10 ml of 48% bromic acid. By concentrating the solution under reduced pressure again, 0.5 g of the title compound was obtained (yield 73%).

Melting point: 225°~227° C.(dec.).

EXAMPLE 13

Preparation of
3-methyl-3,7-diazabicyclo[3.3.0]oct-1(5)-ene
dihydrobromide 3,7-Diazabicyclo[3.3.0]oct-1 (5)-ene dihydrobromide (0.81 g) which was prepared in Preparation 2 was dissolved in water (10 ml). To this solution 35% formaline (0.3 ml) and formic acid (10 ml) were added and refluxed for 4 hours. The solvents were distilled off and the resulting solid was washed with isopropylacohol (20 ml) and ethylether (20 ml) to give the title compound (0.81 g, yield 94%).

Melting point: 185°~187° C.(dec.)

Example 14

Preparation of
3-ethyl-3,7-diazabicyclo[3.3.0]oct-1(5)-ene
dihydrobromide

To a solution of 1-p-toluene sulfonyl-3,4-bis (bromomethyl)-3-pyrroline (3.41 g) in acetonitrile (43 ml), 0.73 ml of 70% ethylamine and anhydrous potassium carbonate (8 g) were added and stirred at room temperature for one hour. The solid was filtered off and the filtrate was purified by silicagel column chromatography (CHCl$_3$—MeOH) to give 3-ethyl-7-p-toluene sulfonyl-3,7-diazabicyclo [3.3.0]oct-1(5)-ene (0.95 g, yield 39%). 0.9 g of this compound was hydrolysized in 20 ml of 48% hydrobromic acid with 1 g of phenol. The hydrolysate was washed with chloroform (30 ml×3) and decolorized with active carbon. The solvent was concentrated and washed with ethanol to give the title compound (0.57 g, yield 62%).

MS m/z (rel. int. %): M+138 (32), 123 (20), 109 (60), 108 (100).

Example 15

Preparation of
3,7-dimethyl-3,7-diazabicyclo[3.3.0]oct-1(5)-ene
dihydrobromide 3,7-Diazabicyclo[3.3.0]oct-1(5)-ene dihydrobromide (0.544 g) was dissolved in formic acid (5 ml) and 36% formaline (5 ml) and then refluxed for 5 hours. The solvents were evaporated under reduced pressure and 20% hydrobromic acid (10 ml) was added to this solid and then refluxed for 30 minutes. Evaporation of solvents and washing with isopropanol to give the title compound (0.54 g, yield 90%).

Example 16

Preparation of
8-methyl-3,8-diazabicyclo[4.3.0]non-1(6)-ene
dihydrobromide (Ie2).

3-Benzyl-3,8-diazabicyclo[4.3.0]non-1(6)-ene dihydrobromide (0.75 g) was refluxed in 85% formic acid (10 ml) and 37% formaline (7 ml) for 5 hours. The solvents were removed under reduced pressure and the solid was washed with isopropanol ethylether (2:1) to give 3-benzyl-8-methyl-3,8-diazabicyclo[4.3.0]non-1(6)-ene dihydrobromide (0.64 g, yield 82%):

$^1$H-NMR (CDCl$_3$, δ ppm): 7.32 (5H, m), 4.02 (4H, s), 3.57 (2H, s), 3.36 (2H, s), 3.21 (3H, s), 2.94 (2H, d, J=5.8 Hz), 2.25 (2H, t, J=5.8 Hz).

The above compound (0.585 g) was stirred in 10% acetic acid in water with 10% palladium-charcoal (0.05 g) under hydrogen stream. After 5 hours the solid was filtered off and 20% hydrobromic acid (5 ml) was added and then the solvents were distilled off. The resulting solid was washed with isopropanol-ethylether (2:1) to obtain the title compound (0.276 g, yield 86%).

$^1$H-NMR (CDCl$_3$, δ ppm): 4.01 (4H, s), 3.30 (2H, s), 3.20 (3H, s), 2.86 (2H, d, J=5.8 Hz), 2.20 (2H, t, J=5.8 Hz).

Example 17

Preparation of
3-methyl-3,8-diazabicyclo[4.3.0]non-1(6)-ene
dihydrobromide (Ie3).

8-p-Toluenesulfonyl-3,8-diazabicyclo[4.3.0]non-1(6)-ene (0.56 g) was methylated with 85% formic acid (10 ml) and 37% formaline (5 ml) by refluxing for 5 hours. The solvents were distilled off. To this solid 48% hydrobromic acid (20 ml) and phenol (1 g) were added and refluxed for 5 hours. The reaction mixture was washed with chloroform (30 ml×4), decolorized with active charcoal. The aqueous layer was concentrated under vacuum and the solid was washed with isopropanol-ether (2:1) to obtain the title compound (0.48 g, yield 83%).

$^1$H-NMR (CD$_3$OD, δ ppm): 4.01 (4H, s), 3.43 (2H, s), 3.16 (3H, s), 2.98 (2H, t, J=5.8 Hz), 2.46 (2H, t, J=5.8 Hz).

Example 18

Preparation of 3,7-dimethyl-3,7-diazabicyclo[3.3.0]oct-1(5)-ene dihydrobromide 3,7-Diazabicyclo[3.3.0]oct-1(5)-ene dihydrobromide (0.82 g) was refluxed with formic acid (10 ml) and 35% formaline (10 ml) for 5 hours. The excess reagents were distilled off and 20% hydrobromic acid (10 ml) was added and refluxed for 1 hour. The solvnet was distilled off and washed with ethanol-ethylether (1:1) to obtain the title compound (0.95 g, yield 86%).

$^1$H-NMR (CD$_3$OD, δ ppm): 4.36 (8H, s), 3.12 (6H, s).

Example 19

Preparation of 3,8-dimethyl-3,8-diazabicyclo[4.3.0]non-1(6)-ene dihydrobromide.

3,8-Diazabicyclo[4.3.0]non-1(6)-ene dihydrobromide (0.57 g) was methylated with formic acid (8 ml) and 37% formaline (8 ml) by refluxing for 5 hours. Work-up as in Example 18 gave the title compound (0.48 g, yield 80%).

$^1$H-NMR (CD$_3$OD, δ ppm): 4.07 (4H, s), 3.45 (2H, s), 3.14 (6H, s), 2.97 (2H, t, J=5.8 Hz), 2.48 (2H, t, J=5.8 Hz).

Example 20

Preparation of 3-methyl-3,7-diazabicyclo[3.3.0]oct-1(5)-ene dihydrobromide.

To a solution of 1-p-toluenesulfonyl-3,4-bis(-bromomethyl)-3-pyrroline (6.1 g) was dissolved in acetonitrile (70 ml), 40% methylamine aqueous solution (1.5 ml) and anhydrous potassium carbonate powder (16 g) were added and stirred for 2 hours at room temperature. The solid was filtered off and the filtrate was purified by silicagel column chromatography to yield 3-methyl-7-p-toluenesulfonyl-3,7-diazabicyclo[3.3.0]oct-1(5)-ene (0.82 g, yield 20%). 0.8 g of this compound and 0.8 g of phenol were refluxed in 48% hydrobromic acid (15 ml) for 5 hours. The reaction mixture was washed with chloroform (20 ml×3), decolorized with active charcoal. The solvent was distilled off and washed with ethanol-ethylether (1:1) to give the title compound (0.5 g, yield 60%).

$^1$H-NMR (CD$_3$OD, δ ppm): 4.42 (4H, s), 4.27 (4H, s), 3.12 (3H, s).

Example 21

Preparation of 8-methyl-3,8-diazabicyclo[4.3.0]non-1(6)-ene dihydrochloride.

To a solution of 2,3-bis (bromomethyl)-1,3-butadiene (4.8 g) and methylenediurethane (3.9 g) in dichloroethane (40 ml), borontrifluoride etherate (0.3 ml) was added. The reaction mixture was refluxed for 10 hours and washed with 10% sodium bicarbonate solution (30 ml×3). The organic phase was filtered though silicagel and evaporation of the solvent to give 1-carboethoxy-4,5-bis(bromomethyl)-1,2,3,6-tetrahydropyridine (6.14 g, yield 90%) which was cyclized with 40% methyl- amine (1.8 ml) and potassium carbonate (15 g) in acetonitrile (50 ml) for 2 hours at room temperature. The solid was filtered off and the filtrate was purified by silicagel column chromatography to give 3-carboethoxy-8-methyl-3,8-diazabicyclo[4.3.0]non-1(6)-ene (2.57 g, yield 68%). This amine was refluxed in 20% hydrochloric acid (50 ml) and evaporation gave the title compound (1.35 g, yield 80%).

$^1$H-NMR (CD$_3$OD, δ ppm): 4.01 (4H, s), 3.32 (2H, s), 3.20 (3H, s), 2.84 (2H, d, J=5.8 Hz), 221 (2H, t, J=5.8 Hz).

By using the diazabicycloamine compounds shown by the general formula (I) which were prepared by the Examples, and quinolone compounds shown by the above formula (A) or (B) and their salts are prepared by the following method.

Use

Use 1

Preparation of 1-cyclopropyl-7-[3,7-diazabicyclo[3.3.0]oct-1(5)-en-3-yl]-6,8-difluoro-1,4-dihydro-4-oxoquinoline-3-carboxylic acid (KR-10679)

The solution of 0.4 g of 1-cyclopropyl-6,7,8-trifluoro-1,4-dihydro-4-oxoquinoline-3-carboxylic acid, 0.8 g of 3,7-diazabicyclo[3.3.0]oct-1(5)-ene dihydrobromide, and 0.8 ml of 1,8-diazabicyclo[5.4.0]undec-7-ene (DBU) in 30 ml of acetonitrile was refluxed in oil bath at the temperature of 100° C. for 8 hours, and this reaction mixture was kept overnight at the room temperature. The product precipitate was filtered off and then the residue was washed with methanol, to obtain 0.35 g of the title compound (yield 67%).

Melting point: 220°~225° C.(dec.)

$^1$H-NMR (CDCl$_3$+CD$_3$COOD, δ ppm): 8.81 (1H, s), 7.87 (1H, d, J=14.2, 1.8 Hz), 4.69 (4H, s), 4.24 (4H, s), 4.01 (1H, m), 1.23 (4H, m).

Use 2

Preparation of 5-amino-1-cyclopropyl-7-[3,7-diazabicyclo[3.3.0]oct-1(5)-en-3-yl]-6,8-difluoro-1,4-dihydro-4-oxoquinoline-3-carboxylic acid (KR-10747)

The solution of 0.4 g of 5-amino-1-cyclopropyl-6,7,8-trifluoro-1,4-dihydro-4-oxoquinoline-3-carboxylic acid, 0.8 g of 3,7-diazabicyclo[3.3.0]oct-1(5)-ene dihydrobromide, and 0.6 ml of 1,8-diazabicyclo[5.4.0]undex-7-ene (DBU) in 40 ml of acetonitrile was refluxed at the reaction temperature of 100° C. for 7 hours. This reaction mixture was kept overnight at the room temperature, and the produced precipitate was filtered and then the residue was washed with ethanol to obtain 0.3 g of the title compound (yield 57%).

Melting point: 220°~225° C.(dec.).

$^1$H-NMR (CDCl$_3$+CD$_3$COOD, δ ppm): 8.69 (1H, s), 4.65 (4H, s), 4.24 (4H, s), 3.91 (1H, m), 1.18 (4H, m).

Use 3

Preparation of 1-cyclopropyl-7-[7-methyl-3,7-diazabicyclo[3.3.0]oct-1(5)-en-3-yl]-6,8-difluoro-1,4-dihydro-4-oxoquinoline-3-carboxylic acid hydrochloride (KR-10755)

0.1 g of 1-cyclopropyl-7-[3,7-diazabicyclo[3.3.0]oct-1(5)-en-3-yl]-6,8-difluoro-1,4-dihydro-4-oxoquinoline-3-carboxylic acid, prepared in the Use 1, was dissolved in the solution mixture of 1 ml of 36% aqueous formaline solution and 1.5 ml of formic acid, and then this reaction mixture was fefluxed at the reaction temperature of 120° C. for 2 hours and it was concentrated under the reduced pressure to remove solvent. 1 ml of isopropyl alcohol and 1 ml of 20% hydrochloric acid was added herein and then it was refluxed more for 1 hour. The solvent was removed under the reduced pressure to remove the solvent and washed with 1:1 mixture solvent of methanol-ether, to obtain 0.082 g of the title compound (yield 78%).

Melting point: 210°~213° C.(dec.).

$^1$H-NMR (CDCl$_3$+CD$_3$COOD, δ ppm): 8.82 (1H, s), 7.85 (1H, d, J=14.3 Hz), 4.83 (2H, m), 4.67 (4H, sr. s), 3.98 (1H, m), 3.89 (2H, m), 3.16 (3H, s), 1.24 (4H, m).

Use 4:

Preparation of 1-cyclopropyl-7-[3,7-diazabicyclo[3.3.0]oct-1(5)-en-3-yl]-5,6,8-trifluoro-1,4-dihydro-4-oxoquinoline-3-carboxylic acid (KR-10758)

0.6 g of 1-cyclopropyl-5,6,7,8-tetrafluoro-1,4-dihydro-4-oxoquinoline-3-carboxylic acid, 1.2 g of 3,7-diazabicyclo[3.3.0]oct-1(5)-ene dihydrobromide and 1.3 ml of 1,8-diazabicyclo[5.4.0]undec-7-ene (DBU) were suspended in 20 ml of acetonitrile, and then the reaction mixture was refluxed for 10 hours. This reaction mixture was kept overnight at the room temperature, and the produced precipitate was filtered and then the residue was washed with ethanol to obtain 0.58 g the title compound (yield 74%).

Melting point: 226°~228° C.(dec.).

$^1$H-NMR (CDCl$_3$+CD$_3$COOD, δ ppm): 8.71 (1H, s), 4.68 (4H, s), 4.18 (4H, s), 4.00 (1H, m), 1.22 (4H, m).

Use 5:

Preparation of (-)-9-fluoro-3-(S)-10-[3,7-diazabicyclo[3.3.0]oct-1(5)-en-3-yl]-7-oxo-2,3-dihydro-7H-pyrido[1.2.3-de]-1,4-benzoxazine-6-carboxylic acid (KR-10759)

0.28 g of (-)-9,10-difluoro-3(S)-methyl-7-oxo-2,3-dihydro-7H-pyrido[1.2.3-de]-1,4-benzoxazine-6-carboxylic acid was dissolved in 3 ml of pyridine, and then 0.5 g of 3,7-diazabicyclo[3.3.0]oct-1(5)-ene dihydrobromice was added herein, next the reaction mixture was refluxed for 10 hours. This reaction mixtrue was concentrated under the reduced pressure three times, and the residue was washed with 1:1 mixture solvent of ethanol-ether to obtain 0.32 g of the title compound (yield 86%).

Melting point: 196° C.(dec.).

$^1$H-NMR (CDCl$_3$+CD$_3$COOD, δ ppm): 8.85 (1H, s), 7.69 (1H, d,J=14.2 Hz), 4.60 (4H, s), 4.51 (1H, m), 4.31 (2H, br.s), 4.21 (4H, s), 1.65 (3H, d,J=6.6 Hz).

Use 6:

Preparation of 1-cyclopropyl-7-[3,7-diazabicyclo[3.3.0]oct-1(5)-en-3-yl-6,8-difluoro-1,4-dihydro-4-oxoquinoline-3-carboxylic acid (KR-10679)

0.28 g of 1-cyclopropyl-6,7,8-trifluoro-1,4-dihydro-4-oxoquinoline-3-carboxylic acid, 0.16 g of 3,7-diazabicyclo-[3.3.0]oct-1(5)-ene and 0.3 ml of 1,8-diazabicyclo-[5.4.0]unde-7-ene (DBU) were suspended in 20 ml of acetonitrile, and then the reaction mixture was fefluxed in oil bath at the reaction temperature of 100° C. for 5 hours. This reaction mixture was kept overnight at the room temperature, the produced precipitate was filtered and the residue was washed with solvent mixture of ethanol-ether (1:1) to obtain 0.3 g of the title compound (yield 80%).

Melting point: 220°~223° C.(dec.).

Use 7:

Preparation of 1-cyclopropyl-6,8-difluoro-7-{3,8-diazabicyclo[4.3.0]-non-1(6)-en-3-yl}-1,4-dihydro-4-oxoquinoline-3-carboxylic acid hydrobromide 0.3 g of 1-cyclopropyl-6,7,8-trifluoro-1,4-dihydro-4-oxoquinoline-3-carboxylic acid and 0.42 g of 8-p-toluenesulfonyl-3,8-diazabicyclo[4.3.0]non-1(6)-ene were dissolved in 20 ml of acetonitrile. 0.3 ml of 1,8-diazabicyclo[5.4.0]undec-7-ene (DBU) were added and then refluxed for 5 hours. The reaction mixture was kept overnight at room temperature. The produced precipitate was filtered and suspended in the mixture of 20 ml of 40% hydrobromic acid and 1 g of phenol. The suspension was refluxed for 5 hours. The reaction mixture was cooled to room temperature and then washed five times with methylene chloride (30 ml×5). The aqueous phase was concentrated under reduced pressue and washed with the ethanol-ethylether (1:1) solvent. 0.34 g of the title compound (yield 68%).

Melting point: 287°~291° C.(dec.).

$^1$H-NMR (CDCL$_3$+CD$_3$COOD, δ ppm): 8.80 (1H, s), 7.88 (1H, d, J=14 Hz), 4.10 (4H, s), 4.00 (1H, m), 3.40 (2H, s, br). 2.94 (2H, t, J=5.8 Hz), 2.31 (2H, t, J=5.8 Hz), 1.25 (4H, m).

Use 8:

Preparation of 1-cyclopropyl-6,8-difluoro-7-{3,8-diazabicyclo[4.3.0]-non-1(6)-en-8-yl}-1,4-dihydro-4-oxoquinoline-3-carboxylic acid 0.3 g of 1-cyclopropyl-6,7,8-trifluoro-1,4-dihydro-4-oxoquinoline-3-carboxylic acid and 0.6 g of 3-benzyl-3,8-diazabicyclo[4.3.0]non-1(6)-ene hydrobromide were suspended in 30 ml of acetonitrile. 0.6 ml of 1,8-diazabicyclo[5.4.0]undec-7-ene (DBU) was added to the suspension. The reaction mixture was refluxed for 5 hours and then kept overnight at room temperature. The produced precipitate was filtered and dissolved in 30 ml of 5% acetic acid in ethanol. After adding 0.5 g of 10% Palladium charcoal, the reaction mixture was stirred under hydrogen stream for 6 hours and then filtered. The filtrate was concentrated under reduced pressure. 0.25 g of the title compound (yield 61%).

Melting point: 270° C.(dec.).

$^1$H-NMR (CDCl$_3$+CD$_3$COOD, δ ppm):8.84 (1H, s), 7.89 (1H, d, J=14. Hz), 4.60 (4H, s), 4.02 (1H, m), 3.41 (2H, s), 2.94 (2H, t, J=5.8 Hz), 2.27 (2H, t, J=5.8 Hz), 1.27 (4H, m).

The antibacterial activity of the quinolone compounds prepared in the previously described Uses according to the present invention is shown in the following Table I and Table II.

The quinolone compounds shown by the above general formula (A) and (B) which were prepared by using the diazabicycloamine compounds shown by the above general formula (I) according to the present invention have much better antibacterial activity against the Gram positive bacteria such as Staphyloccus spp. and Streptococcus spp. than the traditional quinolone compounds such as ofloxacin and norfloxacin, and they have similar or better antibacterial activity than ciprofloxacin.

These quinolone compounds according to the present invention were proved to have superior antibacterial activity to the traditional quinolone antibacterial agents against methicillin resistant *Staphylococcus aureus*.

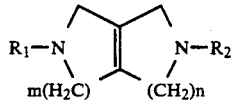

TABLE I

| | | The in vitro antibacterial activity | | | | | | |
|---|---|---|---|---|---|---|---|---|
| | | The minimum inhibition concentration (μg/ml) | | | | | | |
| No. | Bacteria | KR-10679 | KR-10747 | KR-10755 | KR-10758 | KR-10759 | Ciprofloxacin | Ofloxacin |
| 1 | *Streptococcus pyogenes* 308 | 0.098 | 0.391 | 0.195 | 3.125 | 0.781 | 3.125 | 6.25 |
| 2 | *Streptococcus pyogenes* 77 | 0.049 | 0.098 | 0.195 | 0.781 | 0.098 | 0.781 | 1.563 |
| 3 | *Streptococcus faecium* MD 8b | 0.049 | 0.195 | 0.195 | 0.781 | 0.195 | 0.781 | 1.563 |
| 4 | *Staphylococcus aureus* SG 511 | 0.007 | 0.025 | 0.025 | 0.195 | 0.049 | 0.195 | 0.391 |
| 5 | *Staphylococcus aureus* 285 | 0.025 | 0.025 | 0.025 | 0.781 | 0.195 | 0.391 | 0.391 |
| 6 | *Staphylococcus aureus* 503 | 0.013 | 0.025 | 0.025 | 0.781 | 0.195 | 0.391 | 0.391 |
| 7 | *Escherichia coli* O 55 | <0.002 | <0.002 | <0.002 | 0.025 | 0.013 | <0.002 | 0.049 |
| 8 | *Escherichia coli* DC 0 | 0.098 | 0.195 | 0.195 | 0.781 | 0.195 | 0.195 | 0.781 |
| 9 | *Escherichia coli* DC 2 | 0.013 | 0.049 | 0.025 | 0.195 | 0.025 | 0.049 | 0.391 |
| 10 | *Escherichia coli* TEM | <0.002 | 0.013 | 0.007 | 0.098 | 0.025 | <0.002 | 0.098 |
| 11 | *Escherichia coli* 1507E | 0.004 | 0.013 | 0.007 | 0.098 | 0.025 | <0.002 | 0.098 |
| 12 | *Pseudomonas aeruginosa* 9027 | 0.391 | 0.781 | 0.781 | 3.125 | 0.781 | 0.391 | 3.125 |
| 13 | *Pseudomonas aeruginosa* 1592E | 0.391 | 0.391 | 0.781 | 1.563 | 0.391 | 0.195 | 1.563 |
| 14 | *Pseudomonas aeruginosa* 1771 | 0.391 | 0.781 | 0.781 | 3.125 | 0.781 | 0.195 | 1.563 |
| 15 | *Pseudomonas aeruginosa* 1771M | 0.049 | 0.391 | 0.049 | 0.781 | 0.098 | 0.098 | 0.391 |
| 16 | *Salmonella typhimurium* | 0.004 | 0.004 | 0.013 | 0.098 | 0.025 | <0.002 | 0.049 |
| 17 | *Klebsiella aerogenes* 1082E | <0.002 | 0.013 | <0.002 | 0.098 | 0.025 | <0.002 | 0.013 |
| 18 | *Klebsiella aerogenes* 1522E | 0.004 | 0.025 | 0.013 | 0.195 | 0.049 | <0.002 | 0.098 |
| 19 | *Enterobacter cloacae* P 99 | 0.007 | 0.391 | 0.004 | 0.195 | 0.195 | 0.004 | 0.195 |
| 20 | *Enterobacter cloacae* 1321E | <0.002 | <0.002 | <0.002 | 0.049 | 0.013 | <0.002 | 0.025 |

TABLE II

| | The in vitro activity against the methicilline resistant bacteria | | | | |
|---|---|---|---|---|---|
| | | Minimum inhibition concentration (μg/ml) | | | |
| No. | Methicillin resistant strains | KR-10679 | KR-10747 | KR-10759 | Ofloxacin |
| 1 | *Staphylococcus aureus* 88 E | 0.195 | 0.049 | 0.195 | 0.391 |
| 2 | *Staphylococcus aureus* 121 E | 0.098 | 0.049 | 0.098 | 0.195 |
| 3 | *Staphylococcus aureus* 208 E | 0.098 | 0.098 | 0.195 | 0.391 |
| 4 | *Staphylococcus aureus* 256 E | 0.098 | 0.049 | 0.098 | 0.195 |
| 5 | *Staphylococcus aureus* 690 E | 0.049 | 0.025 | 0.049 | 0.195 |
| 6 | *Staphylococcus aureus* 692 E | 0.049 | 0.013 | 0.098 | 0.098 |
| 7 | *Staphylococcus aureus* 693 E | 0.049 | 0.025 | 0.098 | 0.195 |
| 8 | *Staphylococcus aureus* 694 E | 0.098 | 0.049 | 0.195 | 0.195 |
| 9 | *Staphylococcus aureus* 695 E | 0.098 | 0.025 | 0.098 | 0.195 |
| 10 | *Staphylococcus aureus* 697 E | 0.025 | 0.025 | 0.025 | 0.098 |
| 11 | *Staphylococcus aureus* 701 E | 0.098 | 0.098 | 0.098 | 0.195 |
| 12 | *Staphylococcus aureus* 703 E | 0.098 | 0.049 | 0.098 | 0.195 |
| 13 | *Staphylococcus aureus* 705 E | 0.098 | 0.098 | 0.098 | 0.391 |
| 14 | *Staphylococcus aureus* 706 E | 0.049 | 0.049 | 0.098 | 0.195 |
| 15 | *Staphylococcus aureus* 707 E | 0.098 | 0.098 | 0.049 | 0.195 |
| 16 | *Staphylococcus aureus* 708 E | 0.025 | 0.013 | 0.049 | 0.098 |
| 17 | *Staphylococcus aureus* 711 E | 0.049 | 0.013 | 0.098 | 0.098 |
| 18 | *Staphylococcus aureus* 714 E | 0.049 | 0.025 | 0.098 | 0.195 |
| 19 | *Staphylococcus aureus* 725 E | 0.098 | 0.049 | 0.098 | 0.195 |

We claim:
1. A diazabicycloamine of the formula I wherein
  m denotes 1 to 3,
  n denotes 1 to 2 and
  $R_1$ and $R_2$ denote hydrogen or lower alkyl and their salts.
2. A diazabicycloamine as claimed in claim 1, wherein
  m denotes 1 or 2,
  n denotes 1 and
  $R_1$ and $R_2$ denote hydrogen or lower alkyl, with the proviso that $R_1$ and $R_2$ cannot be lower alkyl simultaneously.

* * * * *